(12) United States Patent
Shih

(10) Patent No.: US 6,221,880 B1
(45) Date of Patent: Apr. 24, 2001

(54) COMPOSITION AND METHOD FOR TREATING ALLERGIC DISEASES

(75) Inventor: Neng-Yang Shih, North Caldwell, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/413,025

(22) Filed: Oct. 6, 1999

Related U.S. Application Data

(60) Provisional application No. 60/103,756, filed on Oct. 9, 1998.

(51) Int. Cl.[7] .................. A61K 31/47; A61K 31/445; A61K 31/41; A61K 31/405
(52) U.S. Cl. ................. 514/311; 514/316; 514/382; 514/415
(58) Field of Search ................. 514/311, 415, 514/382, 316

(56) References Cited

U.S. PATENT DOCUMENTS

| | | |
|---|---|---|
| 5,654,316 | 8/1997 | Carruthers et al. . |
| 5,688,960 | 11/1997 | Shankar . |
| 5,691,362 | 11/1997 | McCormick et al. . |
| 5,696,267 | 12/1997 | Reichard et al. . |
| 5,719,156 | 2/1998 | Shue et al. . |
| 5,783,579 | 7/1998 | McCormick . |
| 5,789,422 | 8/1998 | Reichard et al. . |
| 5,795,894 | 8/1998 | Shue et al. . |
| 5,798,359 | 8/1998 | Shue et al. . |
| 6,063,926 | * 5/2000 | Reichard et al. ........... 546/187 |

FOREIGN PATENT DOCUMENTS

| | | |
|---|---|---|
| 480717 | 4/1992 | (EP) . |
| 9926924 | * 6/1999 | (WO) . |

OTHER PUBLICATIONS

C. J. Ohnmacht, Jr. et al, *Annual Rep. in Medicinal Chem.*, 33, 71 (1998).
R. Robertson, *Prostaglandins*, 31, 395 (1986).
J. Musser, et al, *Agents and Actions*, 18, 332 (1986).
J. Piwinski et al, *Annual Rep. in Medicinal Chem.*, 22, 73 (1987).
R. Bell et al, *Annual Rep. in Medicinal Chem.*, 32, 91 (1997).

* cited by examiner

Primary Examiner—William R. A. Jarvis
Assistant Examiner—Vickie Kim
(74) Attorney, Agent, or Firm—Palaiyur S. Kalyanaraman

(57) ABSTRACT

The present invention is directed towards a pharmaceutical composition useful for the treatment allergic rhinitis, asthma and related disorders. In one embodiment, the composition comprises, in combination, a therapeutically effective amount of at least one neurokinin antagonist, and a therapeutically effective amount of at least one 5-lipoxygenase inhibitor.

15 Claims, No Drawings

COMPOSITION AND METHOD FOR TREATING ALLERGIC DISEASES

This application claims the Benefit of U.S. Provisional application Ser. No. 60/103,756 filed Oct. 9, 1998.

FIELD OF THE INVENTION

The present invention generally relates to compositions and methods for treating allergic rhinitis and other respiratory diseases. It specifically discloses compositions which comprise (i) combinations of antagonists of neurokinin receptors and antagonists of leukotriene receptors, and (ii) combinations of antagonists of neurokinin receptors and inhibitors of 5-lipoxygenase, as well as methods for treating the above-noted diseases using such compositions.

BACKGROUND OF THE INVENTION

Neurokinin ("NK") receptors such as the $NK_1$ and the $NK_2$ receptors are found in the central nervous system and the circulatory system and the peripheral tissues of mammals, and are involved in a variety of biological processes. Antagonists of the neurokinin receptors are, therefore, expected to be useful in the treatment or prevention of various mammalian diseases such as, for example, pulmonary disorders such as asthma, cough, bronchospasm, chronic obstructive pulmonary diseases, and airway hyperactivity; skin disorders and itch, for example, atopic dermatitis, and cutaneous wheal and flare; neurogenic inflammatory diseases such as, arthritis, migraine, nociception; CNS diseases such as anxiety, emesis, Parkinson's disease, movement disorders and psychosis; convulsive disorders, renal disorders, urinary incontinence, ocular inflammation, inflammatory pain, and eating disorders such as food intake inhibition; allergic rhinitis, neurodegenerative disorders, psoriasis, Huntington's disease, depression and various disorders such as Crohn's disease. NK, receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma. $NK_1$ and $NK_2$ receptor antagonists have been reported such as, for example, in U.S. Pat. Nos. 5,798,359; 5,795,894; 5,789,422; 5,783,579; 5,719,156; 5,696,267; 5,691,362; 5,688,960; 5,654,316 (all assigned to Schering-Plough Corporation, Madison, N.J.); and in "Recent Advances in Neurokinin Receptor Antagonists", by C. J. Ohnmacht Jr., et al, *Annual Reports in Medicinal Chemistry*, A. M. Doherty Ed., 33, 71–80 (1998).

The products of the 5-lipoxygenase ("5-LO") pathway of arachidonic acid metabolism, particularly the leukotrienes, can mediate bronchoconstriction, mucous secretion, airway mucosal edema, chemotaxis and mobilization of cells into the airway in the inflammatory process of asthma. Therefore, inhibition of 5-LO should help cure, reduce or prevent such diseases. Similarly, leukotriene ("LK") antagonists play a role in treating the multitude of symptoms associated with diseases of the respiratory tract, such as season allergic rhinitis, perennial allergic rhinitis, common colds, sinusitis and concomitant symptoms associated with allergic asthma. The symptoms of such diseases may include sneezing, itching runny nose, nasal congestion, redness of the eye, tearing, itching of the ears or palate, and coughs associated with postnasal drip. A discussion of leukotriene receptors may be found in R. Robertson, *Prostaglandins*, 31, 395 (1986), and a discussion of leukotriene antagonists can be found in J. Musser et al, Agents and Actions, 18, 332 (1986), J. Piwinski et al, *Annual Reports in Medicinal Chemistry*, 22, 73–76 (1987), and R. Bell et al, *Annual Reports in Medicinal Chemistry*, 32, 91 (1997).

It would be highly desirable to enhance the efficacy of the neurokinin antagonists to improve their overall efficacy, as well as to reduce or prevent the above-noted ailments by interfering with the activity of 5-LO and leukotriene receptors.

SUMMARY OF THE INVENTION

The afore-mentioned objective and other objectives and desires are addressed by the present invention which, in one embodiment, provides a composition for treating and preventing allergic rhinitis and other respiratory diseases such asthma, cough, wheezing and the like. The inventive composition comprises, in combination, a therapeutically effective amount of at least one neurokinin antagonist and a therapeutically effective amount of at least one leukotriene antagonist. One or more of the antagonists may be substituted by a pharmaceutically acceptable derivative such as salt, ester, and the like. Optionally, the composition may additionally contain a pharmaceutically acceptable carrier, a decongestant (such as, for example, pseudoephedrine), a cough suppressant (such as, for example, dexrtomethorphan), expectorant (such as, for example, guaifenesin), analgesics (such as, for example, aspirin, ibuprofen and acetaminophen) or mixtures thereof.

Generally, the amount of the neurokinin antagonist content in the inventive composition per unit dosage form is about 1–1,000 milligrams and that of the leukotriene antagonist is about 2–500 milligrams. Preferably, the respective amounts are about 10–500 milligrams and about 5–500 milligrams, and typically the respective amounts are about 50–200 milligrams and 10–50 milligrams.

The present invention additionally provides a composition for treating and preventing allergic rhinitis and other respiratory diseases such asthma, cough, wheezing and the like, the composition comprising, in combination, a therapeutically effective amount of at least one neurokinin antagonist and a therapeutically effective amount of at least one 5-LO inhibitor. One or more of the compounds may be substituted by a pharmaceutically acceptable derivative such as salt, ester, and the like. Additionally, the composition may contain a pharmaceutically acceptable carrier, a decongestant, a cough suppressant, and expectorant, or mixtures thereof.

The invention further provides methods for treating asthma, chronic obstructive pulmonary disease ("COPD"), and allergic disorders, sneezing, itching runny nose, nasal congestion, redness of the eye, tearing, itching of the ears or palate, sinusitis, and coughs associated with postnasal drip symptoms in a mammalian organism in need of such treatment comprising administering the pharmaceutical compositions described above.

DETAILED DESCRIPTION OF THE INVENTION

In one embodiment, the present invention discloses pharmaceutical compositions that are useful in treating and preventing allergic rhinitis, asthma and related disorders. The composition comprises, in combination, a therapeutically effective amount of at least one neurokinin antagonist and a therapeutically effective amount of at least one leukotriene antagonist. One or more of the antagonists may be substituted by a pharmaceutically acceptable derivative such as salt, ester, and the like.

Several neurokinin antagonists that are known currently are useful in the practice of the present invention. Non-limiting examples of such useful neurokinin antagonists include, for example, those belonging to the chemical class of oximes, hydrazones, piperidines, piperazines, aryl alkyl amines, hydrazones, nitroalkanes, amides, isoxazolines, quinolines, isoquinolines, azanorbomanes, naphthyridines, benzodiazepines and the like. Many are disclosed in the U.S. patents cited earlier in this patent application. Preferred NK antagonists are those disclosed in the above-noted U.S. Pat. Nos. 5,798,359; 5,795,894; 5,789,422; 5,783,579; 5,719,156; 5,696,267; 5,691,362; 5,688,960; 5,654,316. The general formula of some of so-disclosed compounds is:

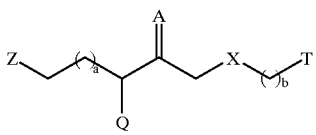

wherein Z is

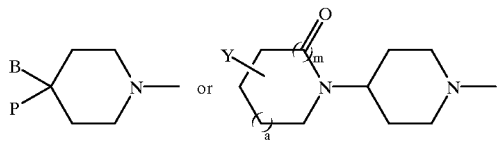

where
B is $OR_2$; $NR_6COR_2$, $CONR_6R_7$ or $NR_2CONR_6R_7$,
m=0 or 1,
P is $R_5$-aryl; or $R_5$-heteroaryl; and
Y is H, $CR_2R_3CO_2R_6$; $CR_2R_3CONR_6R_7$ or $CR_2R_3NR_6COR_2$;
a=b=0, 1 or 2;
Q has the same definitions as P above, with the proviso that P and Q may be the same or different;
A is=N—$OR_1$;=N—$NR_2R_3$; or=$CR_1R_2$;
X is —O—; —$NR_6$—; —$N(R_6)CO$—; or —CO—$NR_6$—;
T is $R_4$-aryl; $R_4$-heteroaryl; $R_4$-cycloalkyl; or $R_2$-bridged cycloalkyl;
$R_1$ is H, $C_1$–$C_6$ alkyl; or $(CH_2)_n$-G where n=1–6,
G is H; $R_4$-aryl; $R_4$-heteroaryl; $COR_6$; $CO_2R_6$; $CONR_6R_7$; CN; $OCOR_6$; $SO_3R_2$;
C(=$NOR_2$)$NR_6R_7$; C(=$NR_2$)$NR_6R_7$, with the proviso that when n≠1, G can additionally be $OR_6$, $NR_6R_7$ or $NR_6(CO)R_7$;
$R_2$ and $R_3$ are independently H or $C_1$–$C_6$ alkyl; $R_4$ and $R_5$ are independently 1, 2 or 3 substituents independently selected from $OR_2$, $OC(O)R_2$, $OC(O)NR_6R_7$, $C_1$–$C_6$ alkyl, H, halogen, $CF_3$, $C_2F_5$, or $OCF_3$; and $R_6$ and $R_7$ are independently selected from H or $C_1$–$C_6$ alkyl, with the proviso that when $R_6$ and $R_7$ are part of $NR_6R_7$ then said $NR6R_7$ may form part of a $C_5$–$C_6$ ring wherein 0–2 ring members are selected from the group consisting of —O—, —S—and —$NR_2$—, with the further proviso that said $C_5$–$C_6$ ring may contain substituents on said ring with said substituents being selected from the group consisting of hydrogen, halogen, —$OR_6$ and —$COOR_6$. Particularly preferred neurokinin antagonists are those disclosed in the above-mentioned United States patents, and belonging to the general formula:

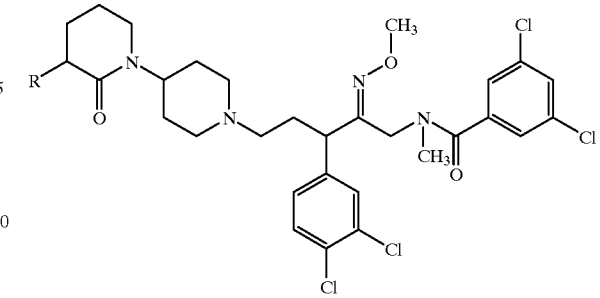

and stereoisomers thereof. More particularly preferred are the stereoisomers with the general formula:

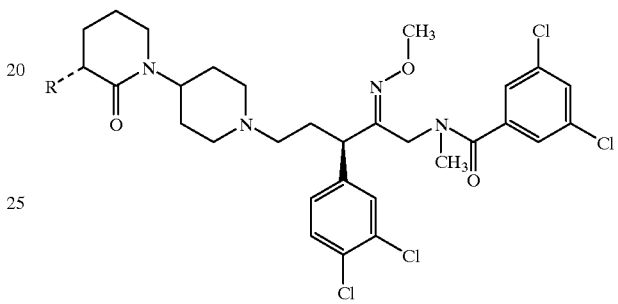

where R is H; $CH_2CONH_2$; $CH_2CONHMe$; $CH_2CONMe_2$ or

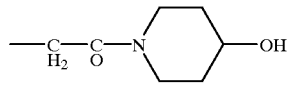

Illustrative non-limiting examples of leukotriene antagonists useful in the practice of the present invention include montelukast (from Merck & Company), pranlukast (from Ono Pharmaceutical Company Limited, CAS Registry Number: 103177-37-3), zafirlukast (from Zeneca Pharmaceuticals; CAS Registry Number: 107753-78-6), CP-195494 (from Pfizer, Incorporated), and the like. The technical name of montelukast is [R-(E)]-1-[[[1-[3-[2-(7- chloro-2-quinolinyl)ethenyl]phenyl]-3-[2-(1-hydroxy-1-methylethyl)phenyl]propyl]thio]methyl]cyclopropaneacetic acid. The technical name of praniukast is N-[4-oxo-2-(1H-tetrazol-5yl)4H-1-benzopyran-8-y1]4-(4-phenylbutoxyybenzamide. The technical name of zafirlukast is [3-[[2- methoxy-4-[[[2-methylphenyl)sulfonyl]amino]carbonyl]phenyl]methyl]-1- methyl-1H-indol-5-yl]-carbamic acid, cyclopentylester, disclosed in EP-00199543. A particularly useful leukotriene is montelukast. Montelukast is a leukotriene D4 antagonist capable of antagonizing the receptors for the cysteinyl leukotrienes. This compound is described in EP 480,717. A preferred pharmaceutically acceptable salt of montelukast is the monosodium salt, also known as montelukast sodium (CAS Registry Number: 151767-02-1).

In another embodiment, this invention discloses other pharmaceutical compositions that are useful in treating and preventing allergic rhinitis, asthma and related disorders. The composition comprises, in combination, a therapeutically effective amount of at least one neurokinin antagonist and a therapeutically effective amount of at least one inhibitor of 5-lipoxygenase. One or more of the compounds may be substituted by a pharmaceutically acceptable derivative such as salt, ester, and the like.

Non-limiting examples of useful neurokinin antagonists are those that are disclosed in the above-cited U.S. patents, including, for example, the compounds where R is H; $CH_2CONH_2$; $CH_2CONHMe$; $CH_2CONMe_2$ or

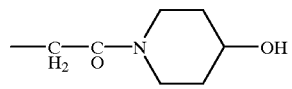

Useful 5-LO inhibitors include, for example, Zileuton (from Abbott Laboratories, CAS Registry Number: 111406-87-2) and Atreluton (from Abbott Laboratories, CAS Registry Number: 154355-76-7). The technical name of Zileuton is N-(1-benzo[b]thien-2-ylethyl)-N-hydroxy-urea. The technical name of Atreluton is N-[(1R)-3-[5-[(4-fluorophenyl)methyl]-2-thienyl]- 1-methyl-2-propynyl]-N-hydroxyurea.

In yet another embodiment, this invention discloses a method for the treatment of asthma, allergic rhinitis, and other allergic disorders, sneezing, itching runny nose, nasal congestion, redness of the eye, tearing, itching of the ears or palate, wheezing, sinusitis, and coughs associated with postnasal drip symptoms in a mammalian organism in need of such treatment comprising administering a pharmaceutical composition which comprises the neurokinin antagonist and the leukotriene antagonist as described above.

In a further embodiment, the present invention teaches a method for the treatment of asthma, allergic rhinitis, and other allergic disorders, sneezing, itching runny nose, nasal congestion, redness of the eye, tearing, itching of the ears or palate, wheezing, sinusitis, and coughs associated with postnasal drip symptoms in a mammalian organism in need of such treatment comprising administering a pharmaceutical composition which comprises the neurokinin antagonist and the 5-LO inhibitor as described above.

In the pharmaceutical compositions and methods of the present invention, the active ingredients will typically be administered in admixture with suitable pharmaceutical diluents, excipients or carriers (collectively referred to herein as carrier materials) suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. neurokinin antagonism, leukotriene antagonism, 5-LO inhibition and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 750 milligrams, more preferably from about 0.01 to about 500 milligrams, and typically from about 0.01 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day. The amount and frequency of the administration will be regulated according to the judgment of the attending clinician. A generally recommended daily dosage regimen for oral administration may range from about 0.04 milligrams to about 4,000 milligrams per day, in single or divided doses.

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

It will be apparent to those skilled in the art that many modifications, variations and alterations to the present disclosure, both to materials and methods, may be practiced. Such modifications, variations and alterations are intended to be within the spirit and scope of the present invention.

What is claimed is:

1. A pharmaceutical composition comprising, in combination, a therapeutically effective amount of at least one neurokinin antagonist or a pharmaceutically acceptable derivative thereof, and a therapeutically effective amount of at least one leukotriene antagonist or a pharmaceutically acceptable derivative thereof, wherein said neurokinin antagonist is a compound having the general formula:

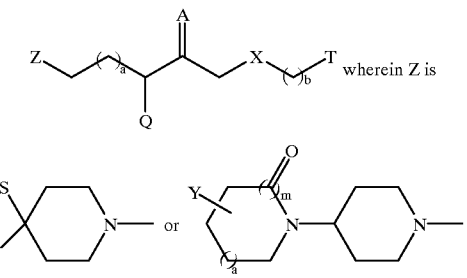

where B is $OR_2$; $NR_6COR_2$, $CONR_6R_7$ or $NR_2CONR_6R_7$, m=0 or 1,

P is $R_5$-aryl; or $R_5$-heteroaryl; and

Y is H, $CR_2R_3CO_2R_6$; $CR_2R_3CONR_6R_7$ or $CR_2R_3NR_6COR_2$, a=b=0, 1 or 2;

Q has the same definitions as P above, with the proviso that P and Q may be the same or different;

A is=N—$OR_1$;=N—$NR_2R_3$; or=$CR_1R_2$;

X is —O—; —$NR_6$—; —N($R_6$)CO—; or —CO—$NR_6$—;

T is $R_4$-aryl; $R_4$-heteroaryl; $R_4$-cycloalkyl; or $R_2$-bridged cycloalkyl;

$R_1$ is H, $C_1$–$C_6$ alkyl: or $(CH_2)_n$-G where n=1–6,

G is H; $R_4$-aryl; $R_4$-heteroaryl; $COR_6$;$CO_2R_6$; $CONR_6R_7$; CN; $OCOR_6$; $SO_3R_2$; C(=$NOR_2$)$NR_6R_7$;

C(=NR$_2$)NR$_6$R$_7$, with the proviso that when n≠1, G can additionally be OR$_6$, NR$_6$R$_7$ or NR$_6$(CO)R$_7$;

R$_2$ and R$_3$ are independently H or C$_1$–C$_6$ alkyl;

R$_4$ and R$_5$ are independently 1, 2 or 3 substituents independently selected from OR$_2$, OC(O)R$_2$, OC(O)NR$_6$R$_7$, C$_1$–C$_6$ alkyl, H, halogen, CF$_3$, C$_2$F$_5$, or OCF$_3$; and R$_6$ and R$_7$ are independently selected from H or C$_1$–C$_6$ alkyl, with the proviso that when R$_6$ and R$_7$ are part of NR$_6$R$_7$ then said NR$_6$R$_7$ may form part of a C$_5$–C$_6$ ring wherein 0–2 ring members are selected from the group consisting of —O—, —S— and —NR$_2$—, with the further proviso that said C$_5$–C$_6$ ring may contain substituents on said ring, with said substituents being selected from the group consisting of hydrogen, halogen, —OR$_6$ and —COOR$_6$.

2. The pharmaceutical composition of claim 1, wherein said neurokinin antagonist or its pharmaceutically acceptable derivative is present in amounts of 1–1,000 milligrams per unit dosage of said pharmaceutical composition.

3. The pharmaceutical composition of claim 1, wherein said neurokinin antagonist or its pharmaceutically acceptable derivative is present in amounts of 10–500 milligrams per unit dosage of said pharmaceutical composition.

4. The pharmaceutical composition of claim 1, wherein said neurokinin antagonist or its pharmaceutically acceptable derivative is present in amounts of 50–200 milligrams per unit dosage of said pharmaceutical composition.

5. The pharmaceutical composition of claim 1, wherein said leukotriene antagonist or its pharmaceutically acceptable derivative is present in amounts of 2–500 milligrams per unit dosage of said pharmaceutical composition.

6. The pharmaceutical composition of claim 1, wherein said leukotriene antagonist or its pharmaceutically acceptable derivative is present in amounts of 5–100 milligrams per unit dosage of said pharmaceutical composition.

7. The pharmaceutical composition of claim 1, wherein said leukotriene antagonist or its pharmaceutically acceptable derivative is present in amounts of 10–50 milligrams per unit dosage of said pharmaceutical composition.

8. The pharmaceutical composition of claim 1, wherein said neurokinin antagonist is a compound having the general formula:

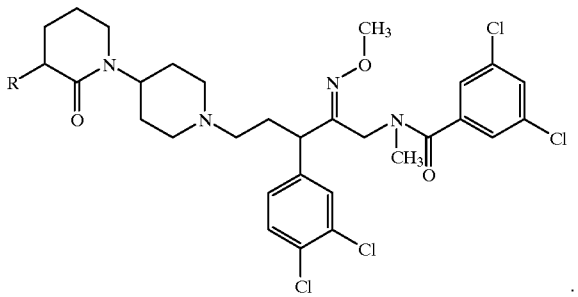

and stereoisomers thereof, where R=H; CH$_2$CONH$_2$; CH$_2$CONHMe; CH$_2$CONMe$_2$ or

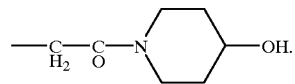

9. The pharmaceutical composition of claim 1, wherein said neurokinin antagonist is a compound having the general formula:

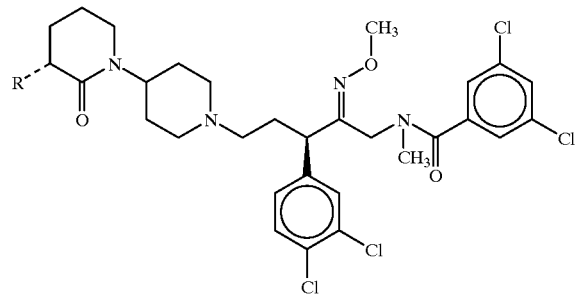

where R is H; CH$_2$CONH$_2$; CH$_2$CONHMe; CH$_2$CONMe$_2$ or

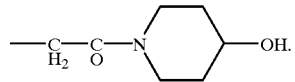

10. The pharmaceutical composition of claim 9, wherein said neurokinin antagonist is the compound where R is CH$_2$CONH$_2$.

11. The pharmaceutical composition of claim 9, wherein said neurokinin antagonist is the compound where R is CH$_2$CONHMe.

12. The pharmaceutical composition of claim 11, wherein said leukotriene antagonist is selected from the group consisting of montelukast, montelukast sodium, pranlukast, zafirlukast and CP-195494.

13. The pharmaceutical composition of claim 12, wherein said leukotriene antagonist is montelukast sodium.

14. The pharmaceutical composition of claim 1, additionally containing one or more materials selected from the group consisting of a pharmaceutically acceptable carrier, a decongestant, a cough suppressant and an expectorant.

15. A method for the treatment of asthma, allergic rhinitis, chronic obstructive pulmonary disease, sneezing, itching runny nose, nasal congestion, redness of the eye, tearing, itching of the ears or palate, wheezing, coughs associated with postnasal drip symptoms and respiratory disorders associated with allergy in a mammalian organism in need of such treatment, said treatment comprising: administering a pharmaceutical composition comprising, in combination, a therapeutically effective amount of at least one neurokinin antagonist or a pharmaceutically acceptable derivative thereof and a therapeutically effective amount of at least one leukotriene antagonist or a pharmaceutically acceptable derivative thereof, wherein said neurokinin antagonist is a compound stated in claim 1.

* * * * *